United States Patent
Durand et al.

(10) Patent No.: US 11,040,200 B2
(45) Date of Patent: Jun. 22, 2021

(54) SYSTEMS THAT USE FEEDBACK-BASED NEURAL STIMULATION FOR BLOOD PRESSURE CONTROL

(71) Applicant: CASE WESTERN RESERVE UNIVERSITY, Cleveland, OH (US)

(72) Inventors: Dominique M. Durand, Solon, OH (US); Grant McCallum, South Euclid, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 234 days.

(21) Appl. No.: 15/571,296

(22) PCT Filed: May 5, 2016

(86) PCT No.: PCT/US2016/030901
§ 371 (c)(1),
(2) Date: Nov. 2, 2017

(87) PCT Pub. No.: WO2016/179354
PCT Pub. Date: Nov. 10, 2016

(65) Prior Publication Data
US 2018/0110989 A1  Apr. 26, 2018

Related U.S. Application Data

(60) Provisional application No. 62/157,091, filed on May 5, 2015, provisional application No. 62/322,853, filed on Apr. 15, 2016.

(51) Int. Cl.
*A61N 1/36* (2006.01)
*A61N 1/05* (2006.01)

(52) U.S. Cl.
CPC ........ *A61N 1/36117* (2013.01); *A61N 1/0551* (2013.01); *A61N 1/36125* (2013.01); *A61N 1/36135* (2013.01)

(58) Field of Classification Search
None
See application file for complete search history.

(56) References Cited

U.S. PATENT DOCUMENTS 5,662,698 A * 9/1997 Altman ................. A61N 1/056
607/123
7,191,016 B2 * 3/2007 Marshall .............. A61N 1/0568
607/122

(Continued)

FOREIGN PATENT DOCUMENTS

| WO | 2008080062 A2 | 7/2008 |
| WO | 2009012502 A1 | 1/2009 |
| WO | 2014044283 A1 | 3/2014 |

OTHER PUBLICATIONS

Lewitus, D. L., et al., Biohybrid Carbon Nanotube/Agarose Fibers for Neural Tissue Engineering. Advanced Functional Materials. Wiley-V C H Verlag Gmbh & Co. KGAA. DE. vol. 21. No. 14. Jul. 22, 2011 (Jul. 22, 2011) pp. 2624-2632. XP001564165. ISSN: 1616-301X. DOI: 10.1002/ADFM.201002429 [retrieved on May 5, 2011] the whole document.

(Continued)

*Primary Examiner* — Kennedy Schaetzle
(74) *Attorney, Agent, or Firm* — Tarolli, Sundheim, Covell & Tummino LLP

(57) ABSTRACT

The present disclose generally relates to a system that controls blood pressure based on feedback-based neural stimulation. The system can include an electrode implantable within a nerve (e.g., an intra-fascicular electrode). The system can also include a hermetically-sealed electronics module connected to the electrode to record data related to neural activity from the nerve. The data related to the neural activity is indicative of the blood pressure. The system can also include an external device to communicate with the (Continued)

hermetically-sealed electronics module to receive and analyze the data related to the neural activity.

5 Claims, 4 Drawing Sheets

(56) References Cited

U.S. PATENT DOCUMENTS

| | | | |
|---|---|---|---|
| 9,555,583 B1* | 1/2017 | Dirk | A61N 1/0551 |
| 10,238,875 B2* | 3/2019 | Mashiach | A61N 1/0551 |
| 2008/0140195 A1* | 6/2008 | Su | A61B 5/04001 |
| | | | 623/11.11 |
| 2010/0113895 A1* | 5/2010 | Cho | A61B 5/0537 |
| | | | 600/302 |
| 2010/0268055 A1* | 10/2010 | Jung | A61B 5/04001 |
| | | | 600/377 |
| 2011/0230747 A1 | 9/2011 | Rogers et al. | |
| 2014/0067000 A1* | 3/2014 | Higgins | A61L 31/06 |
| | | | 607/2 |
| 2015/0216483 A1* | 8/2015 | Sevcencu | A61B 5/0402 |
| | | | 600/301 |
| 2017/0182312 A1* | 6/2017 | Durand | A61N 1/0558 |

OTHER PUBLICATIONS

International Search Report corresponding to International App. No. PCT/US2016/030901, dated Aug. 1, 2016, pp. 1-16.

\* cited by examiner

SYSTEMS THAT USE FEEDBACK-BASED NEURAL STIMULATION FOR BLOOD PRESSURE CONTROL

RELATED APPLICATIONS

This application claims the benefit of U.S. Provisional Application No. 62/157,091, entitled "NEURAL MODULATION OF THE CAROTID SINUS NERVE (CSN)," filed May 5, 2015. This application also claims the benefit of U.S. Provisional Application No. 62/322,853, entitled "SYSTEMS AND METHODS THAT USE FEEDBACK-BASED NEURAL STIMULATION FOR BLOOD PRESSURE CONTROL," filed Apr. 15, 2016. These provisional applications are hereby incorporated by reference in their entireties for all purposes.

TECHNICAL FIELD

The present disclosure relates generally to blood pressure control and, more specifically, to systems and methods that use feedback-based neural stimulation for blood pressure control.

BACKGROUND

Hypertension (also referred to as high blood pressure) generally refers to a medical condition characterized by persistent elevation of the pressure exerted by circulating blood on arterial walls. Hypertension has become a major human health problem, affecting as much as 30% of the population in the United States. Long-term hypertension is a major risk factor for coronary artery disease, stroke, heart failure, peripheral vascular disease, vision loss, chronic kidney disease, and the like.

In most cases, the root cause of hypertension remains unknown. However, there is mounting evidence that many forms of hypertension are due to the sympathetic nervous system. Based on this evidence, renal denervation has been developed as a minimally invasive procedure where nerves in the wall of the renal artery are ablated. In theory, this ablation leads to a reduction in sympathetic afferent and efferent activity to the kidney and, ultimately, a decrease in blood pressure. However, clinical trials have shown renal denervation to be ineffective at controlling blood pressure.

SUMMARY

The present disclosure relates to blood pressure control and, more specifically, to systems and methods that use feedback-based neural stimulation for blood pressure control.

In one aspect, the present disclosure can include a system that controls blood pressure based on feedback-based neural stimulation. The system can include an electrode implantable within a nerve (e.g., an intra-fascicular electrode). The system can also include a hermetically-sealed electronics module connected to the electrode to record data related to neural activity from the nerve. For example, the hermetically-sealed electronics module can include a low noise neural amplifier to aid in the recording of the data related to the neural activity. The data related to the neural activity is indicative of the blood pressure. The system can also include an external device to communicate with the hermetically-sealed electronics module to receive and analyze the data related to the neural activity.

In another aspect, the present disclosure can include a method for feedback-based neural stimulation for blood pressure control. The method can include recording chemoreceptor data or baroreceptor data related to blood pressure of a patient. Based on the chemoreceptor data or the baroreceptor data, a stimulation can be configured to reduce the blood pressure. The configured stimulation can be delivered to a nerve by an electrode implanted within the nerve.

In a further aspect, the present disclosure can include a system that controls blood pressure based on feedback-based neural stimulation. The system can include an electrode implantable within a fascicle of a nerve; and an implantable hermetically-sealed electronics module connected to the electrode to record data related to neural activity in the nerve indicative of blood pressure to generate a stimulation based on the data. The electrode can deliver the stimulation to at least a portion of fibers in the nerve. The hermetically-sealed electronics module can include a low noise neural amplifier to aid in the recording of the data related to the neural activity.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
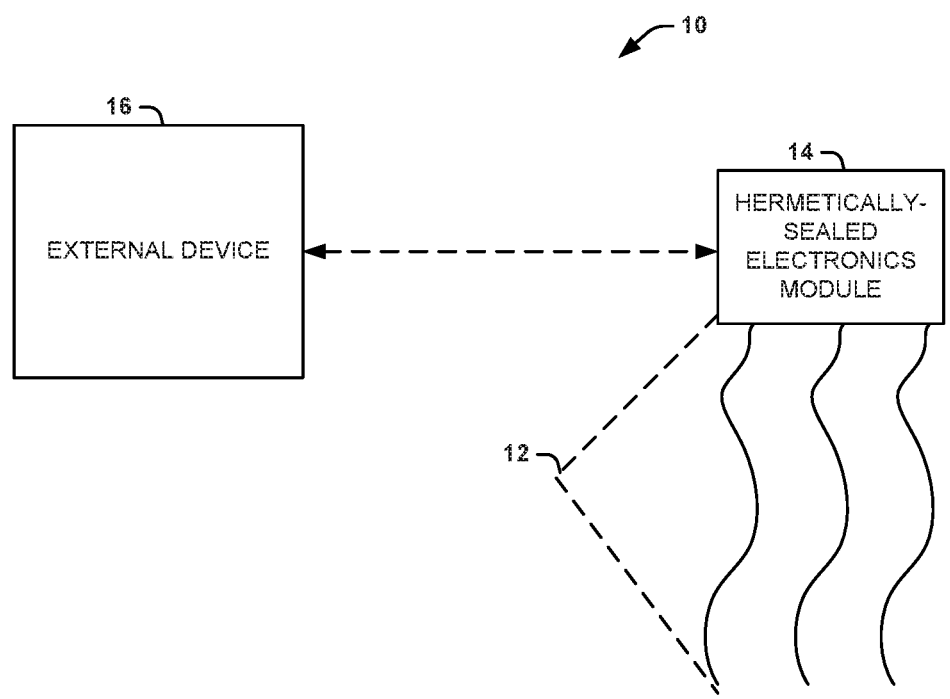
FIG. 1 is a schematic diagram showing a system that provides feedback-based neural stimulation for blood pressure control in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the terms "hypertension" and "high blood pressure" can refer to a medical condition in which the blood pressure in a patient's arteries is persistently elevated.

As used herein, the term "neural stimulation" can refer to the activation or inhibition (also referred to as "block") of a nerve through an external source. In some instances, the external source can be an electrical stimulator that can deliver an electrical signal that can be used for neural stimulation. In some instances, neural stimulation can be used for "blood pressure control" to reduce blood pressure. For example, blood pressure can be reduced by blocking an afferent nerve with a sinusoidal waveform and/or a pulse waveform.

As used herein, the term "feedback-based neural stimulation" can refer to a detected signal that is fed back to a generator of the neural stimulation to control the neural stimulation.

As used herein, the term "electrode" can refer to a conductor through which a current enters or leaves a non-metallic medium. In some instances, the conductor can be substantially encased in an insulator with one or more contacts exposed to deliver or receive the current to the non-metallic medium. In some instances, the electrode can be an intrafascicular electrode sized and dimensioned to be placed within a fascicle of a nerve.

As used herein, the term "wire" can refer to a conductor (metallic or non-metallic) sized and dimensioned on the microscale or less. In other words, the wire can have an unconstrained longitudinal size (or length) and a lateral size (or diameter) constrained as 100 µm or less. In some instances, the lateral size can be constrained to 1 µm or less. In other instances, the lateral size can be constrained to 1 µm or less. In still other instances, the lateral size can be constrained to 0.1 µm or less. In further instances, the lateral size can be constrained to 0.01 µm or less. In still further instances, the lateral size can be constrained to 0.001 µm or less.

As used herein, the term "insulator" can refer to a material with internal electric charges that do not flow freely, making it nearly impossible to conduct an electric current under the influence of an electric field. In other words, an insulator can be generally non-conductive.

As used herein, the term "contact" can refer to a conductive area of an electrode. For example, a contact can be an area of the conductor not covered by the insulator.

As used herein, the conductor being "substantially" encased in the insulator can refer to the entire conductor being encased in the insulator but for one or more contacts. For example, when the conductor is a wire, the wire can be about 98%, about 95%, about 93%, about 90%, about 80%, about 70%, or about 50% or less encased by the insulator.

As used herein, the term "nerve" can refer a cell that employs electrical and chemical signals to transmit information. As an example, the term "nerve" can be used to refer to one or more components of the peripheral nervous system. A nerve can be a peripheral nerve that includes one or more fascicles or bundles of nerve fibers (motor, sensory, and/or autonomic) surrounded by perineurium. An intrafascicular electrode can be inserted within the perineurium of a fascicle within a peripheral nerve.

As used herein, the term "autonomic nervous system" can refer to a part of the peripheral nervous system that influences the function of internal organs and includes both afferent (sensory) fibers and efferent (motor) fibers. The autonomic nervous system includes the sympathetic nervous system (quick response mobilizing system, "fight or flight") and the parasympathetic nervous system (more slowly activated dampening system, "rest and digest").

As used herein, the term "hermetically-sealed" can refer to the quality of a container being airtight at least against the flow of gasses and/or liquids.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to blood pressure control. Recently, several potential treatments for blood pressure control have been proposed, including bilateral renal nerve denervation. However, each of these potential treatments has proven unsuccessful at consistently controlling high blood pressure. These potential treatments may fail due to a lack of understanding of the neural mechanisms underlying high blood pressure, particularly the modalities of the afferent and efferent fibers, and the inability to create a direct-chronic interface with these afferent and efferent fibers. The present disclosure alleviates these issues by employing an electrode that can be inserted within a fascicle of a nerve to stimulate (activate and/or block) and/or record activity within the nerve.

The present disclosure describes a closed loop system that regulates blood pressure using an electrode capable of both recording and stimulating (activating or blocking conduction from the nerve). The electrode can be connected to a hermetically-sealed electronics module that can receive a recording of efferent nerve activity and direct the delivery of an afferent stimulation to activate and/or block conduction in the afferent fibers based on the recorded activity (e.g., the hermetically-sealed electronics module can include a low noise neural amplifier to aid in the recording of the data related to the neural activity). For example, the electrode can apply low frequency stimulation to activate conduction in the nerve or a high frequency stimulation to block conduction in the nerve. Accordingly, the present disclosure relates, more specifically, to systems and methods that use feedback-based neural stimulation for blood pressure control.

III. Systems

One aspect of the present disclosure can include a system 10 (FIG. 1) that can provide feedback-based neural stimulation for blood pressure control. For example, a stimulation can activate or block conduction in a nerve based on recorded activity related to blood pressure. The system 10 can include one or more electrodes 12 and a hermetically-sealed electronics module 14. In some instances, the system 10 can also include an external device 16 (e.g., with computing/control capabilities) that can communicate with the hermetically-sealed electronics module 14. Advantageously, the system 10 can deliver the neural stimulation configured in response to data recorded and correlated to high blood pressure. It will be understood that high blood pressure is only an example application. The system 10 can be applied to control any acid-base imbalance disease. In some instances, an algorithm to control the feedback-based neural stimulation can reside in the hermetically-sealed electronics module 14. In other instances, the algorithm to control the feedback-based neural stimulator can reside in the external device 16. In still other instances, the algorithm to control the feedback-based neural stimulation can reside in part in the hermetically-sealed electronics module and in part in the external device 16.

The one or more electrodes 12 can be implantable within a nerve. For example, the nerve can be the carotid sinus nerve, the glossopharyngeal nerve, or any other nerve that includes one or more fibers that control blood pressure. For example, the one or more electrodes 12 can include one or more intrafascicular electrodes. The one or more electrodes 12 can be connected to the hermetically-sealed electronics module 14. In some instances, the hermetically-sealed electronics module 14 can be configured for implantation. In other words, components of the hermetic seal can be biocompatible. In some instances, the electrode 12 can be a single electrode implanted within the fascicle. In other instances, the electrode 12 can be a plurality of electrodes implanted within different fascicles, but each connected to the hermetically-sealed electronics module.

Figure 2:
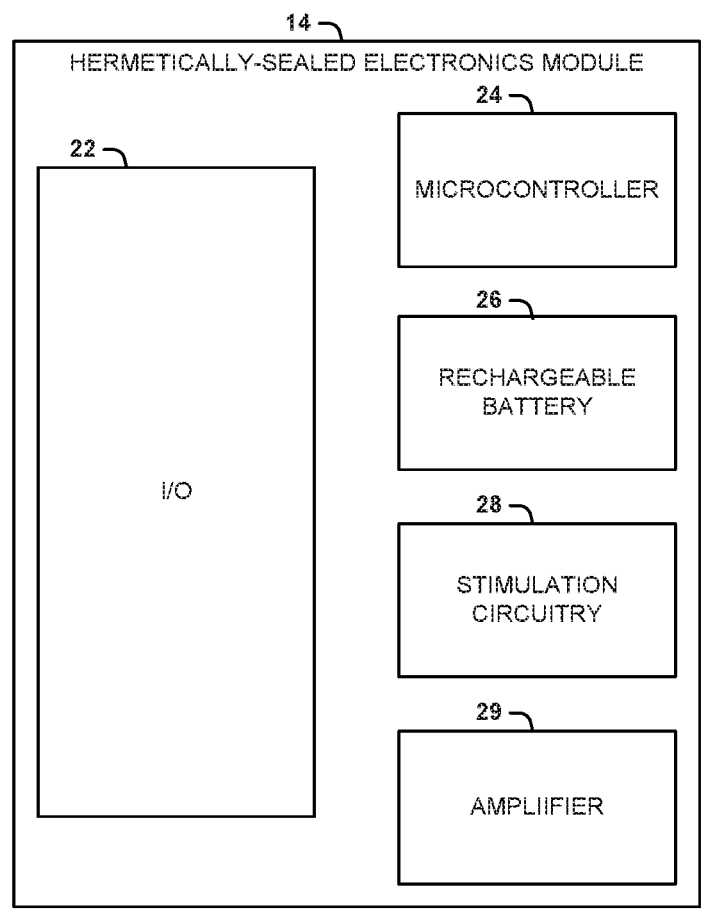
FIG. 2 is a schematic diagram of an example of the hermetically-sealed electronics module that can be used in FIG. 1.

FIG. 2 shows an example of hermetically-sealed electronics module 14 that can be used by the system 10. As shown in FIG. 2, the hermetically-sealed electronics module 14 can include an input/output (I/O), which can include a receiver, a transmitter, and/or a transceiver. The I/O 22 can receive inputs relate to detection of one or more signals indicative of blood pressure. The signals can include neural signals or other signals related to blood pressure. For example, the neural signals can be related to chemoreceptor activity and/or baroreceptor activity. In some instances, the hermetically-sealed electronics module 14 can include one or more recording amplifiers that can enhance the detected signals. The hermetically-sealed electronics module 14 can also include a microcontroller 24, which can receive the detected (and, in some instances, amplified) signals. In some instances, the microcontroller 24 can relate the signals to the blood pressure. For example, the microcontroller 24 can signal stimulation circuitry 28 to deliver a stimulation to the one or more electrodes 12 (in some instances, based on the blood pressure). The microcontroller 24 can, in some instances, determine parameters for the stimulation based on the detected signals. The parameters can include strength, amplitude, shape, polarity, time, duration, and the like. The I/O 22 can deliver the configured stimulus to the one or more electrodes 12 for application to the nerve. The hermetically-sealed electronics module 14 can also include a rechargeable battery 26. The hermetically-sealed electronics module 14 can also include one or more recording amplifiers 29 to aid in the recording of neural activity. For example, at least one of the recording amplifiers 29 can include a low noise neural amplifier to aid in the recording of the data related to the neural activity.

In some instances, the hermetically-sealed electronics module 14 can communicate with an external device 16. In some instances, the communication can be across a wireless connection. In other instances, the communication can be across a wired connection. In still other instances, the communication can be across a wired and a wireless connection. For example, the external device 16 can be an external controller that can receive the detected signals and analyze the signals. The external device 16 can communicate with the hermetically-sealed electronics module 14 to configure the stimulus based on the analysis of the signals. Additionally, the external device 16 can produce and/or download control signals and upload data, such as recordings.

The one or more electrodes 12 can receive the configured stimulation from the hermetically-sealed electronics module 14 and apply the stimulation to the nerve. In some instances, the one or more electrodes 12 can also provide the signals that include recorded data related to neural activity to the hermetically-sealed electronics module 14.

The one or more electrodes 12 can be sized and dimensioned for insertion within a fascicle of a nerve to stimulate (activate and/or block) and/or record within the nerve. In some instances, the one or more electrodes 12 can include a conductive wire substantially encased in an insulator. The conductive wire can have a low cross-sectional surface area so not to generate a strong immune response. For example, the conductive wire can have an unconstrained longitudinal (length) size and a lateral (diameter) sized and dimensioned on the microscale or less. In some instances, the diameter size can reduce or eliminate damage to a nerve while minimizing an immune response to each electrode 12. The conductive wire can have a cross-sectional profile that is circular, oval, square, rectangular, or the like. The cross-sectional profile and/or the diameter of the conductive wire can vary depending on a particular application for the one or more electrodes 12. Additionally, the conductive wire can be made of one or more materials capable of conducting a current therethrough. The one or more materials can be metallic or non-metallic. Examples of such materials can include platinum, iridium, gold, silver, tungsten, carbon, combinations, oxides, or the like.

In some instances, the conductive wire can have a flexural rigidity (FR) that is close in magnitude to that of the surrounding nerve. Generally, the FR relates to the amount of resistance offered when bending. The FR can be expressed as a product of the material's Young's Modulus (E) and a second moment of inertia ($I_{x,y}$) about an axis in the units of N–m$^2$. Accordingly, a lower FR corresponds to greater flexibility. One example material that exhibits a FR close to that of a nerve is carbon nanotubes. A conductive wire of carbon nanotubes exhibits a FR closer in magnitude to that of the surrounding nerve biological medium. Accordingly, in some instances, the conductive wire can include carbon nanotubes.

The fascicle is surrounded by a protective membrane, referred to as the perineurium. Accordingly, for the one or more electrodes 12 to be inserted within the fascicle, the perineurium must be penetrated. An example of the structure and function of an electrode 12, as well as a delivery system for the electrode is shown and described in more detail in International Patent Application PCT/US2015/024855, entitled "Neural Electrodes and Methods for Implanting Same" by Durand, et al., which is hereby incorporated by reference in its entirety. Electrodes 12 inserted in this manner using the delivery system shown and described can be inserted by penetrating the perineurium without substantially injuring the perineurium. Additionally, it would be advantageous to establish a tight seal between each penetrating electrode and the perineurium. For example, carbon nanotubes have been shown to adhere to the perineurium membrane, thereby forming a tight seal between the perineurium and the carbon nanotubes.

The insulator can include one or more insulating materials that generally do not permit transmission of charge. In some examples, the insulating material can be one of parylene, silicone, or plasma-deposited amorphous carbon. In one example, the insulating material can comprise a 2 micron layer of plasma-modified silicone. At least one biocompatible agent can be adsorbed to an outer surface of the insulating material. The biocompatible agent can include any biological or organic molecule that improves the biocompatibility of the one or more electrodes 12. For example, the insulator can include silicon infused with collagen, which increases cell adhesion.

Figure 3:
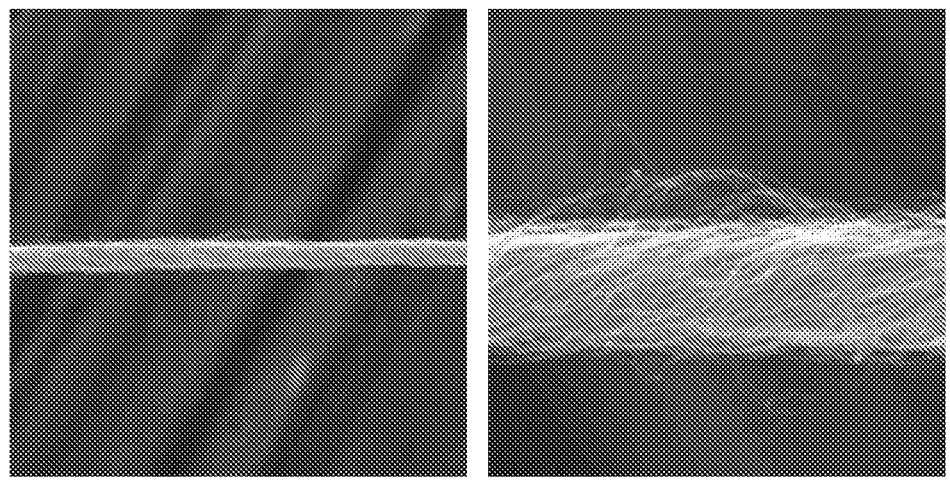
FIG. 3 shows photographs with different magnifications of an exemplary electrode that can be used by the system of FIG. 1.

An example electrode 12 is shown in FIG. 3. As shown in FIG. 3, the electrode is microsized and matched to the molecular and mechanical properties of the nerve. The conductive wire is made of carbon nanotubes with a silicon insulator infused with collagen. The conductive wire has a very low FR and a high compatibility with neural tissue. For example, carbon nanotubes have been shown to promote the growth of neurons and to improve neural signal recordings.

IV. Methods

Figure 4:
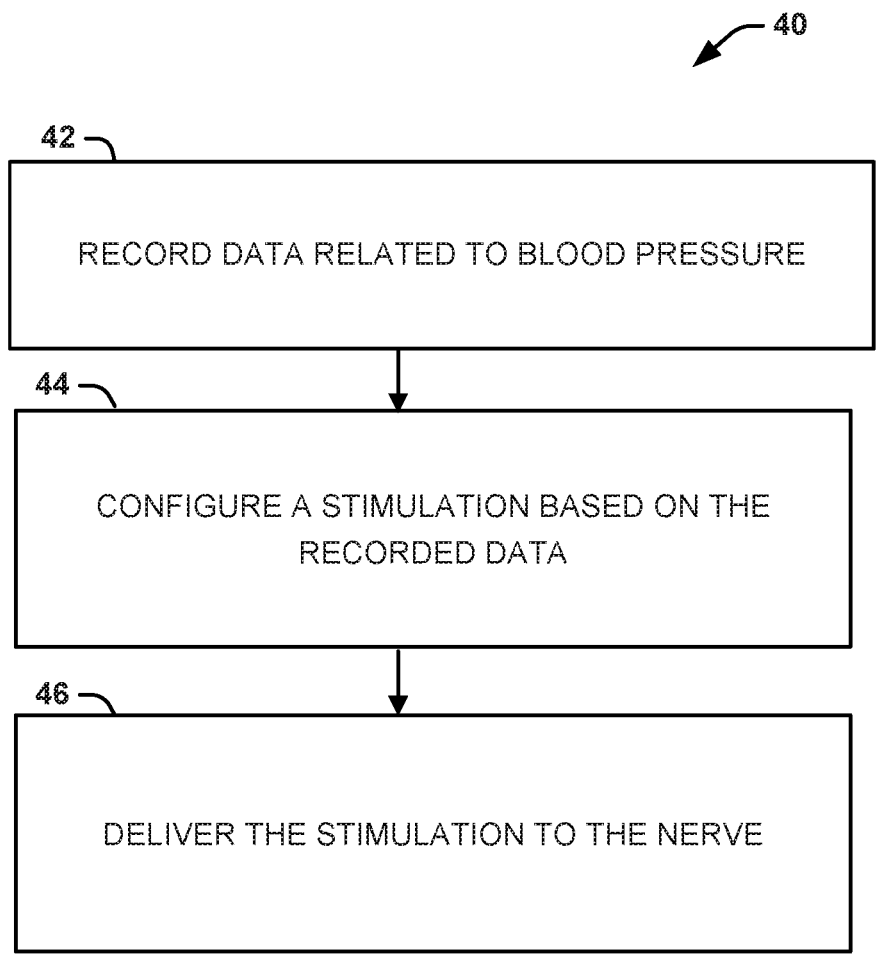
FIG. 4 is a process flow diagram illustrating a method for providing blood pressure control through feedback based neural stimulation according to another aspect of the present disclosure.

Another aspect of the present disclosure can include a method 40 (FIG. 4) for using feedback based neural stimulation for blood pressure control. The method 40 can be executed using the system 10 shown in FIG. 1 and described above. Advantageously, the electrode(s) 12 of the system 10 can be implanted within a fascicle of a nerve for recording and stimulation to facilitate feedback-based neural stimulation. In other words, the method 40 can be used for blood pressure control safely without mechanical or immune reactions, thereby increasing patient safety and increasing the potential for clinical adoption.

The method 40 can generally include the steps of: recording data related to blood pressure (Step 42); configuring a stimulation based on the recorded data (Step 44); and delivering the stimulation to a nerve by an electrode implanted within the nerve (Step 46). The method 40 is illustrated as process flow diagrams with flowchart illustrations. For purposes of simplicity, the method 40 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 30.

At Step 42, data related to blood pressure can be recorded (e.g., by one or more electrodes 12 and/or by one or more sensors located outside the nerve). In some instances, the data can be related to neural activity that can be recorded by an implanted intra-fascicular electrode (e.g., one or more electrodes 12). The neural activity can be related to chemoreceptor activity and/or baroreceptor activity, which can be correlated to high blood pressure. In other instances, the data can include one or more recordings from sensors located outside the nerve (e.g., one or more external or implantable probes). The sensor recordings can be correlated to the recorded neural activity.

At Step 44, a stimulation can be configured (e.g., by hermetically-sealed electronics module 14 and/or external device 16) based on the recorded data. In other words, the stimulation can be configured based on feedback related to the data to reduce the blood pressure of the patient. In some instances, the stimulation can be configured at a low frequency to activate conduction in the nerve. In other instances, the stimulation can be configured at a low frequency to block conduction in the nerve.

At Step 46, the stimulation can be delivered to the nerve (e.g., by one or more electrodes 12). For example, the stimulation can be delivered to afferent fibers within the nerve, such as chemoreceptor afferent fibers or baroreceptor afferent fibers. In some instances, the stimulation can be delivered by one or more electrodes located within the same nerve as the recording electrode. For example, the stimulation can be delivered by the same electrode as the recording electrode. In other instances, the stimulation can be delivered by one or more electrodes located within a different nerve than where the recording took place (but both the stimulating electrodes and the recording electrode are connected to the hermetically-sealed electronics module 14).

From the above description, those skilled in the art will perceive improvements, changes and modifications. Such improvements, changes and modifications are within the skill of one in the art and are intended to be covered by the appended claims.

The following is claimed:

1. A system comprising:
an electrode implantable within a nerve, wherein the electrode is configured for recording data related to efferent nerve activity within the nerve and stimulation of afferent fibers within the nerve, wherein the electrode comprises an exposed conducting portion and an insulated portion comprising silicone with absorbed collagen an external device;
a hermetically-sealed electronics module comprising a microcontroller connected to the electrode, stimulation circuitry, and a rechargeable battery, wherein the electrode records the data related to the efferent nerve activity and sends the data related to the efferent nerve activity to the microcontroller and the microcontroller decides whether action is necessary based on the data related to the efferent nerve activity and sends the data related to the efferent nerve activity to the external device, wherein the data related to the efferent nerve activity corresponds to chemoreceptor data or baroreceptor data that is indicative of blood pressure, and the stimulation circuitry configures a signal to be applied by the electrode for the stimulation of the afferent fibers based on the microcontroller deciding that the action is necessary; wherein
the external device is configured to communicate with the hermetically-sealed electronics module, to receive and analyze the data related to the efferent nerve activity from the microcontroller of the hermetically-sealed electronics module to determine whether the data related to the efferent nerve activity correlates to high blood pressure,
wherein the external device communicates through the microcontroller to the stimulation circuitry to configure a stimulation to be applied by the electrode to stimulate and/or block conduction within the afferent fibers within the nerve when the analyzed data related to the efferent nerve activity corresponds to the high blood pressure reading.

2. The system of claim 1, wherein the electrode comprises a carbon nanotube wire and the insulated portion covers the entire carbon nanotube wire except for the exposed conducting portion.

3. The system of claim 1, wherein the electrode comprises a maximum flexural rigidity of a same magnitude as that of the nerve.

4. The system of claim 1, wherein the electrode comprises a thickness of 100 µm or less.

5. A system comprising:
an electrode implantable within a fascicle of a nerve, wherein the electrode is configured for recording data related to efferent nerve activity within the nerve and stimulation of afferent fibers within the nerve, wherein the electrode comprises an exposed conducting portion and an insulated portion comprising silicone with absorbed collagen; and
an implantable hermetically-sealed electronics module comprising a microcontroller connected to the electrode, stimulation circuitry, and a rechargeable battery, wherein the electrode records the data related to the efferent nerve activity and sends the data related to the efferent nerve activity to the microcontroller and the microcontroller decides whether an action is necessary based on the data related to the efferent nerve activity, wherein the data related to the efferent nerve activity corresponds to chemoreceptor data or baroreceptor data that is indicative of blood pressure, and wherein the stimulation circuitry configures a signal to be applied by the electrode for the stimulation of the afferent fibers when the microcontroller decides that the action is necessary when the efferent nerve activity is determined to correlate to a high blood pressure and the electrode receives the signal and delivers the stimulation to the afferent fibers within the nerve.

* * * * *